United States Patent [19]

Kanno

[11] Patent Number: 4,658,655
[45] Date of Patent: Apr. 21, 1987

[54] FLUID SAMPLING DEVICE FOR MEDICAL USE

[75] Inventor: Michio Kanno, Miyoshi, Japan

[73] Assignee: Terumo Kabushiki Kaisha, Tokyo, Japan

[21] Appl. No.: 830,233

[22] Filed: Feb. 14, 1986

Related U.S. Application Data

[63] Continuation of Ser. No. 596,512, Apr. 4, 1984, abandoned.

[30] Foreign Application Priority Data

Jul. 26, 1983 [JP] Japan ................. 58-136154

[51] Int. Cl.⁴ ............................................. G01N 1/14
[52] U.S. Cl. ........................ 73/863.85; 73/863.84; 73/863.71; 128/765; 128/766
[58] Field of Search ............ 73/863.81, 863.83–863.86, 73/863.71, 863.72; 128/637, 760, 762–766, 912, DIG. 3; 604/4, 5, 6, 32, 83, 85, 248

[56] References Cited

U.S. PATENT DOCUMENTS

| | | | |
|---|---|---|---|
| 2,674,265 | 4/1954 | Dennis | 128/764 X |
| 2,886,000 | 5/1959 | Clegg | 73/863.86 X |
| 2,999,499 | 9/1961 | Willet | 604/83 |
| 3,429,186 | 2/1969 | Price et al. | 73/863.71 X |
| 3,467,095 | 9/1969 | Ross | 604/6 |
| 3,513,845 | 5/1970 | Chestnut et al. | 604/4 |
| 3,906,935 | 9/1975 | Raia et al. | 128/762 |
| 4,127,111 | 11/1978 | Drolet | 128/760 |
| 4,245,509 | 1/1981 | Mody et al. | 73/863.86 |
| 4,246,899 | 1/1981 | Loseff | 128/764 X |
| 4,258,717 | 3/1981 | Bisera et al. | 604/4 X |
| 4,397,335 | 8/1983 | Doblar et al. | 604/32 X |
| 4,416,280 | 11/1983 | Carpenter et al. | 604/83 X |
| 4,425,116 | 1/1984 | Bilstad et al. | 604/6 X |

FOREIGN PATENT DOCUMENTS

| | | |
|---|---|---|
| 808268 | 10/1948 | Fed. Rep. of Germany . |
| 2639161 | 3/1977 | Fed. Rep. of Germany . |
| 57-11221 | 3/1982 | Japan . |

OTHER PUBLICATIONS

"Effect of Venous Occlusion in Arterial Blood Flow"; *Surgery*; vol. 31, #1; p. 57; Jan. 1952.
"Intra-Arterial Transfusion in the Treatment of Severe Injury"; *The Journal of Bone and Joint Surgery*; pp. 112–113, vol. 37B, No. 1, Feb. 1955; Ronald Cowie.

Primary Examiner—Stewart J. Levy
Assistant Examiner—Tom Noland
Attorney, Agent, or Firm—Frishauf, Holtz, Goodman & Woodward

[57] ABSTRACT

In a medical device for sampling fluid, typically blood, two check valves are arranged in series in a fluid sampling line to cause the fluid to flow in one direction and a fluid sampler is connected to the fluid line between the two check valves through an adaptor, thereby preventing the fluid from flowing from the sampler to the inlet of the upstream check valve. The inlet of the upstream check valve is connectable to a plurality of source fluid lines through a switching valve for selective communication.

2 Claims, 10 Drawing Figures

FIG. 2 Prior Art
FIG. 2a
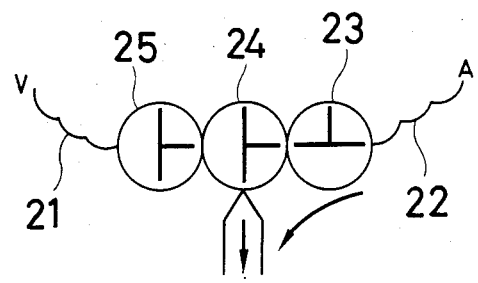
FIG. 2b
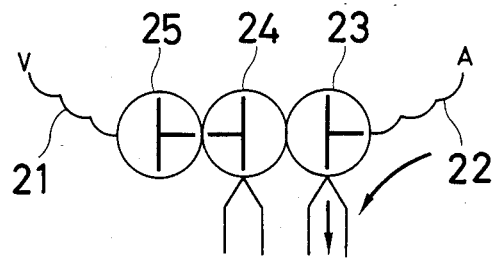
FIG. 2c
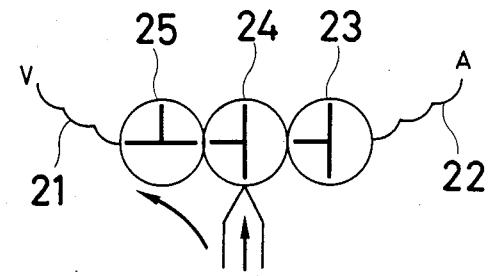
FIG. 2d
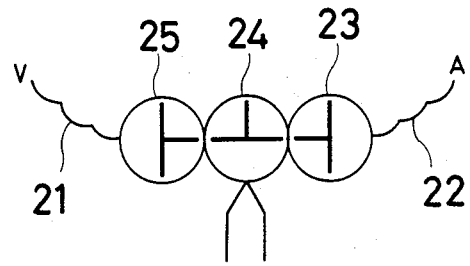

FLUID SAMPLING DEVICE FOR MEDICAL USE

This application is a continuation-in-part, of application Ser. No. 596,512, filed Apr. 4, 1984 and now abandoned.

BACKGROUND OF THE INVENTION

1. Field of the Invention

The present invention relates to a fluid sampling device for medical use capable of taking samples of blood or other fluids from a fluid line such as in an extracorporeal circulation circuit in a medically safe manner.

2. Prior Art

In the past, the following methods have been used to collect blood samples from extracorporeal blood circulation circuits for use in various blood tests.

(1) In dialysis circuits (dialyzers), a hypodermic needle is usually inserted in a rubber medication port in the line. A sample is aspirated with a syringe.

(2) In oxygenator circuits, such rubber medication ports are not used because the internal line pressure is often high. Normally, three-way stopcocks are placed at the sample collection point, and blood samples are collected by switching of the stopcocks. Another reason for not using rubber medication ports is that sample collection is more frequent than on a dialyzer circuit. Because blood gas components, $O_2$ and $CO_2$ concentrations, concentrations of $K^+$, $Na^+$, $Cl^-$, $Ca^{++}$ and other ions, protein concentrations, hematocrit, and other values are frequently measured, there is concern over the durability of the rubber cap. But when three-way stopcocks are used, there is also frequently concern over the possibility of therapeutic problems arising as a result of incorrect operation. Another disadvantage of both methods (1) and (2) is that the syringe must be attached directly to the collection site, which has been inconvenient. For instance, to take a sample from a circuit in which blood is drained from the patient by gravity, one must reach down almost to the level of the floor to carry out the collection procedure.

(3) A method that improves upon the drawbacks of methods (1) and (2) has been devised, whereby slender tubes are led out from the sample collection site to a place where the procedure can be easily carried out. This shall be described later in detail with reference to the figure.

However, one disadvantage common to methods (1), (2), and (3) is the possibility of introducing air into the extracorporeal circulation line as a result of incorrect operation. Operation of the three-way stopcocks in methods (2) and (3) in particular is difficult, making these extremely dangerous in the hands of someone unfamiliar with their use. A similar error may invite the danger of arterial blood, which is under high pressure, spurting from the sampling line.

SUMMARY OF THE INVENTION

It is, therefore, an object of the present invention to provide an easy-to-use device for sampling a fluid, typically blood from a fluid line such as in an extracorporeal blood circuit, and especially an oxygenator circuit, without the danger of introducing air into the circuit.

According to a first aspect of the invention, there is provided a fluid sampling device for medical use comprising a fluid line, flow direction control means including two check valves arranged in series in the fluid line for passing fluid through the line in a given direction, and fluid sampling means connected to the fluid line between said two check valves for sampling the fluid therefrom. Then the reverse flow of the fluid from said sampling means to the inlet side of said flow direction control means is effectively prevented.

According to a second aspect of the invention, there is provided a fluid sampling device for medical use comprising a fluid line, a flow direction control means including two check valves arranged in series in the fluid line for passing fluid through the line in a given direction, fluid sampling means connected to the fluid line between said two check valves for sampling the fluid therefrom, and switching means provided at the inlet of said flow direction control means and connected to a plurality of source fluid lines for selective communication therewith. Then the reverse flow of the fluid from said sampling means to the inlet of said flow direction control means is effectively prevented.

Preferably, as the fluid sampling means, an adaptor is connected to the fluid line between the two check valves to permits the liquid-tight attachment of a fluid sampler. The pressure of the check valves required for opening the flow line is preferably at least 500 mmHg.

BRIEF DESCRIPTION OF THE DRAWINGS

FIGS. 2a-2d illustrate as components making up FIG. 2 the operational procedures of a conventional blood sampling device;

DESCRIPTION OF THE PREFERRED EMBODIMENTS

The fluid sampling device for medical use of the present invention will be described in further detail. An oxygenator circuit is presented herein by way of illustration and not by way of limination.

Figure 1:
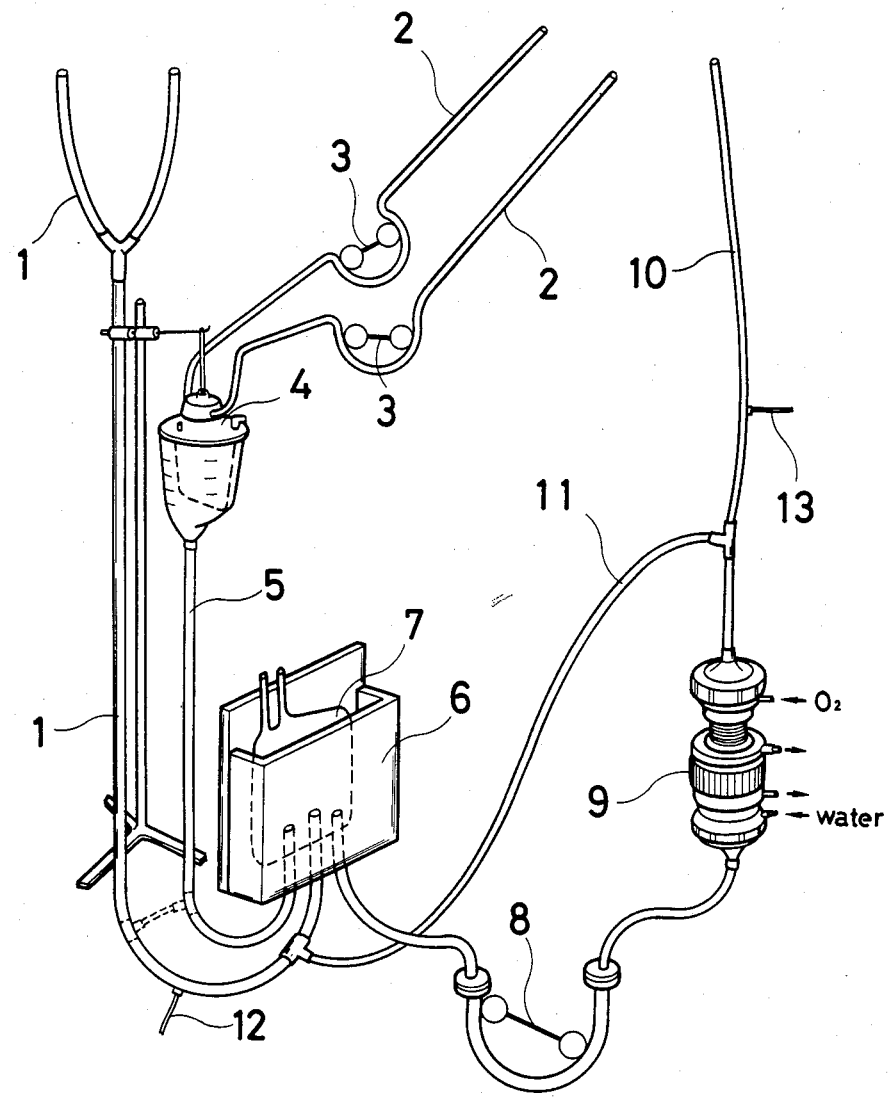
FIG. 1 is a perspective view of an oxygenator arrangement.

FIG. 1 illustrates a portion of an oxygenator circuit. Blood bled from the patient's vena cava is fed to a venous reservoir 7 through a venous drainage line 1. Blood from the surgical field is pumped through aspiration lines 2 by pumps 3 into a cardiotomy reservoir 4 and then fed to the venous reservoir 7 through a line 5. The reservoir 7 is held in volume-regulating means 6. The blood is sent by a pump 8 to an oxygenator 9 equipped with a heat exchanger where it is oxygenated. The blood is returned to the patient's body via an arterial infusion line 10. An optional circulation line 11 is connected between the lines 1 and 10.

In an oxygenator circuit as shown in FIG. 1, venous blood in the drainage line 1 must be sampled in order to determine the condition of the patient while arterial blood in the infusion line 10 must be sampled to ascertain whether the blood has been sufficiently oxygenated and whether blood delivery by the oxygenator is adequate. Blood samples must be collected from both the drainage and infusion lines 1 and 10 for such blood testing purposes. As explained earlier, conventional sampling methods (1) and (2) described above are fraught with problems, which has led to the development of method (3).

This prior art sampling method will be briefly described with reference to FIG. 2.

Slender sampling tubes 21 and 22, which are depicted at 12 and 13 in FIG. 1, are connected to the venous drainage line (to be referred to V line) and the arterial infusion line (to be referred to A line), respectively. Three three-way stopcocks 23, 24, and 25, at the left, center, and right as viewed in FIG. 2, are arranged in series between the tubes 21 and 22. Each of the three-way stopcocks is provided with a blood sampling port.

Initially, the left and right three-way stopcocks 23 and 25 are in the "off" position, that is, not connected to the A or V line as shown in FIG. 2d. To collect a sample of arterial blood from the A line, a dummy syringe is attached to the center three-way stopcock 24, and the right stopcock 23 is turned to the "on" position, that is, connected to A line as shown in FIG. 2a. The unfresh blood that has been present within the sampling tube 22 on the A line side is in this way withdrawn by means of the dummy syringe. Next, the center stopcock 24 is turned to the "off" position while, a sampling syringe is attached to the right stopcock 23 to collect a sample of fresh blood as shown in FIG. 2b. When sample collection is over, the right stopcock 23 is turned off, the left stopcock 25 is turned on, and the blood within the dummy syringe is returned to the V line via the tube 21 as shown in FIG. 2c. Sampling is terminated by turning all the three-way stopcocks to the "off" positions. The procedure is exactly the same when taking blood samples from the V line, except that the blood collected in the dummy syringe is returned to the V line.

Compared with method (1) and (2) described earlier, this prior art method has the advantage that all the manipulations can be carried out within easy reach. However, as already noted, operation of the three-way stopcocks is complicated and requires practice. Moreover, in the step shown in FIG. 2c, if stopcock 23 is turned on rather than stopcock 25, air is delivered to the A line or arterial side, presenting the risk of a major complication such as obstruction of capillaries in the brain.

As just explained, to collect samples of fresh blood, the sample must be taken after first removing the blood already in the sampling lines connected to the V line and/or A line. The blood removed must be later returned, not to the A line, but to the V line, which has a debubbling function. A mistake in executing this step is extremely dangerous and can be life-threatening. Yet, this problem has not been resolved in the device shown in FIG. 2. Furthermore, the method of operation is complicated, inviting error.

The present invention thus aims to provide a sampling device that completely avoids the risks of air entry in all situations, particularly in circuits such as oxygenator circuits from which the entry of air must be prevented, and that is safe, yet simple to operate, not involving the complexities of three-way stopcocks.

Figure 3:
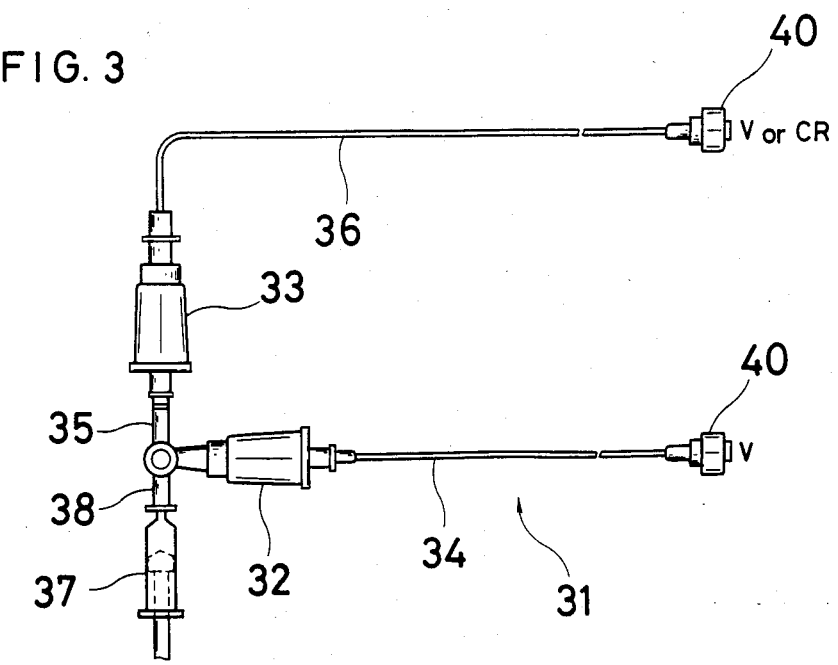
FIG. 3, 4, and 5 illustrate different embodiments of the sampling device of the present invention in which venous blood is sampled, arterial blood is sampled, and venous or arterial blood is selectively sampled from an oxygenator circuit as shown in FIG. 1, respectively.
Figure 4:
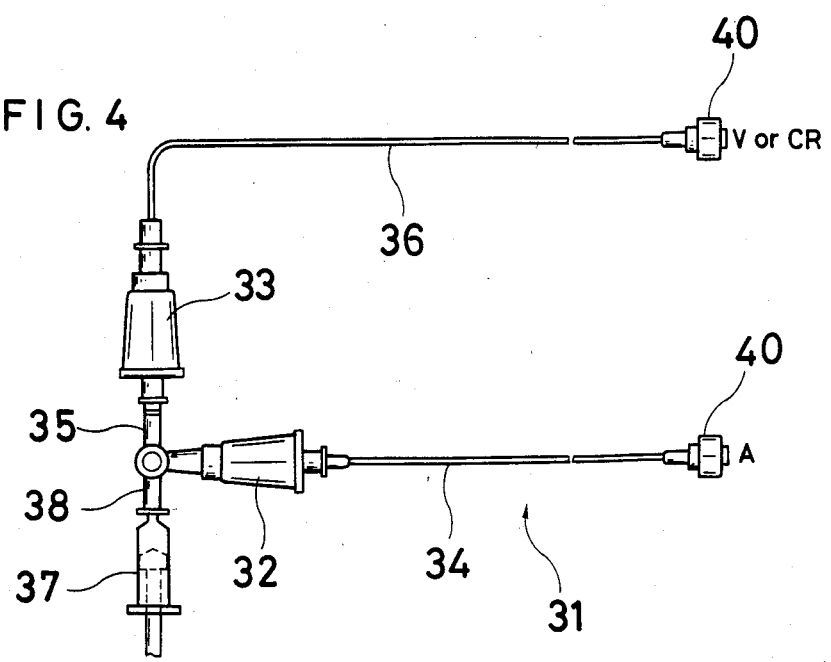
Figure 5:
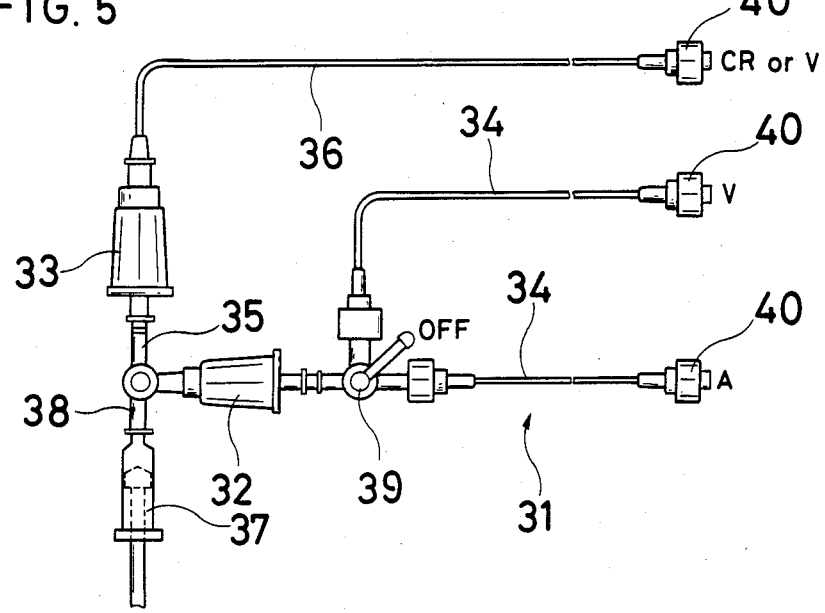

FIGS. 3 and 4 show embodiments in which there is just one line through which the fluid to be sampled for testing flows. FIG. 5 shows a further embodiment in which there are two such lines.

FIG. 3 is a sampling device of the present invention for sampling venous blood in an oxygenator circuit as shown in FIG. 1. A sampling line 31 corresponds to the line 12 connected to the venous drainage line 1 in FIG. 1. Fluid flow direction control means is provided by arranging two check or nonreturn valves 32 and 33 in series and at suitable intervals, causing the fluid to flow in a single direction (flow from upstream valve 32 to downstream valve 33). The flow direction control means includes a blood inflow portion 34, a blood sampling portion 35, and a blood discharge portion 36. The inflow portion 34 is connected through a connector 40 to the V line (or the venous drainage line 1 in FIG. 1), and the discharge portion 36 is connected through a connector 40 to the V line side, i.e., the V line on the cardiotomy reservoir CR (depicted at 4 in FIG. 1), this side having a debubbling function that prevents problems even should air enter the line. The sampling portion 35 has an adaptor 38 which permits the fluid-tight attachment of a suitable sampler in the form of a syringe 37.

FIG. 4 shows another embodiment of the sampling device according to the present invention for sampling arterial blood in an oxygenator circuit as shown in FIG. 1. The construction is almost identical to that of the device shown in FIG. 3, the only difference being that the blood inflow portion 34 is to be connected to the A line or the blood infusion line 10 in FIG. 1 for arterial blood sampling. As will be explained later, the discharge portion 36 is not connected to the A line because air must not be delivered to the A line side by the pumping of syringe 37. In sampling arterial blood, the preferred check valve 32 is one which is not opened by the arterial pressure, but by the negative pressure caused by suction of the syringe 37. If the check valves 32, 33 are opened by the arterial pressure, there is created a circuit where the arterial blood, that is, oxygenated blood can be circulated to the cardiotomy reservoir 4, resulting in reduced oxygenation efficiency.

FIG. 5 shows a further embodiment used when there are a plurality of sampling fluid sources. This is constructed substantially as shown in FIGS. 3 and 4. In this embodiment, switching means in the form of a three-way stopcock 39 is provided at the inlet side of the upstream check valve 32 and connected to the downstream ends of blood inflow portions 34. In the embodiment shown in FIG. 5, one inflow portion 34 may be coupled to the A line while the other inflow portion 34 may be coupled to the V line. When sampling is not necessary, the stopcock 39 may be set to the "off" position. If desired, switching means 39 may of course be so designed as to have a larger number of connections.

Figure 6:
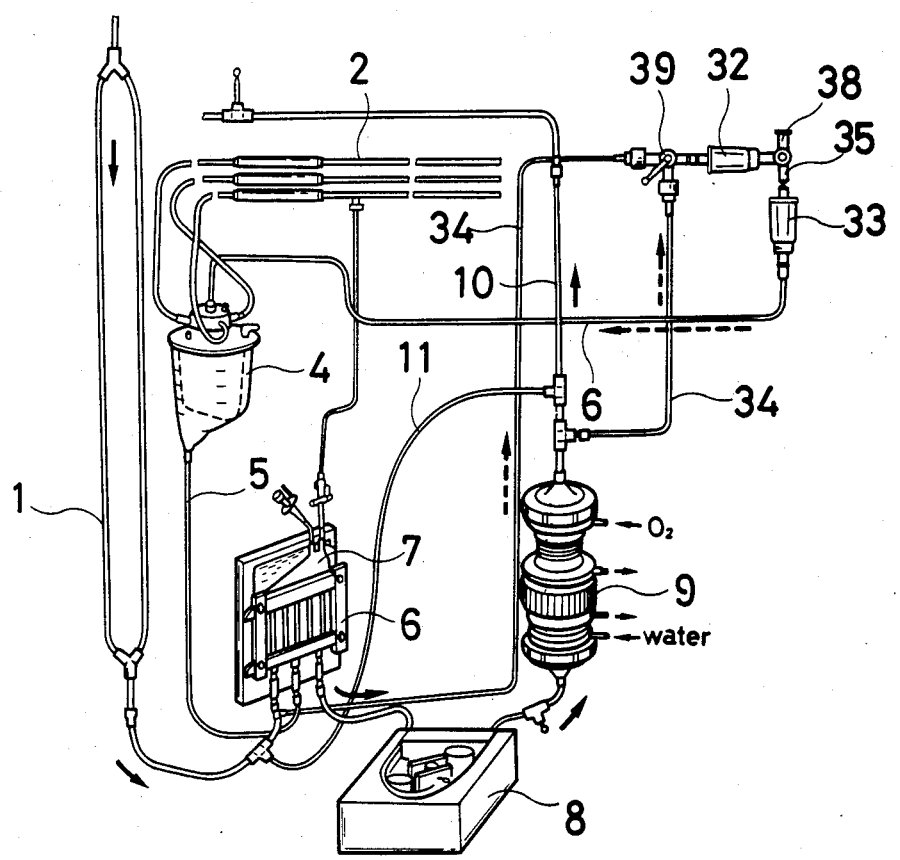
FIG. 6 illustrates an overall arrangement in which the fluid sampling device of FIG. 5 is incorporated in the oxygenator circuit of FIG. 1.

FIG. 6 shows an overall arrangement in which the fluid sampling device shown in FIG. 5 is incorporated in the oxygenator circuit shown in FIG. 1. The blood flows in the direction of solid arrows, and the sampling blood flows as shown by dashed arrows. Coupling to the A and V lines is via connectors 40 in the embodiments shown in FIGS. 3, 4, and 5.

The check or non-return valves used in the fluid sampling device of the invention are well known in the art and commercially available. If the upstream check valve 32 has a resistance of at least 300 mmHg and preferably at least 500 mmHg to blood flow, then it can prevent the spurting out of arterial blood under arterial pressure even when the syringe 37 is removed.

Figure 7:
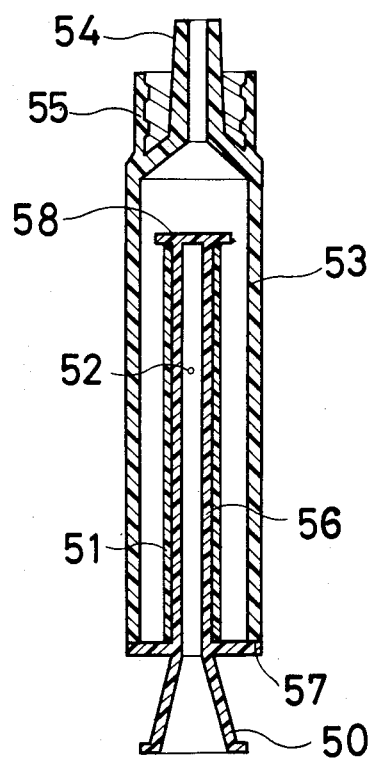
FIG. 7 is a cross-sectional view of a preferred example of the check valve used in the present invention.

The check valves employed in the present invention are intended for the formation of a one-way flow of fluid. This one-way flow is achieved by arranging two such valves in series to establish a pumping action. The upstream check valve 32 is provided for the purpose of preventing the blood once sucked in the syringe 37 from entering the source line when it is returned to the circuit. The downstream check valve 33 is provided for the purpose of ensuring that only the blood in the inflow portion 34, that is, the blood to be examined is sampled by means of the syringe 37 without being contaminated with the blood in the discharge portion 36. One most desirable example of the check valve is disclosed in Japanese Patent Publication No. 11221/82, and shown in FIG. 7.

An outer tube 53 made of a synthetic resin such as polypropylene is provided at one end with a primary fitting portion 54 having, for example, a Luer taper such as to fit into a Luer connector on the infusion line. The fit with the Luer connector becomes even tighter when there is integrally provided a supplementary fitting portion 55 comprising an annular wall formed about the outside circumference of primary fitting portion 54, on the inside surface of which wall are formed threads. Giving the fitting portion of the outer tube a Luer configuration is desirable when the Luer connector on the infusion line can be connected to the Luer tip configuration on an injector. An inner tube 56 forms a projection extending from the closed side at the other end of the outer tube into the interior of the outer tube, and is made of a synthetic resin such as polypropylene. At lease one pore 52 is perforated in the wall of inner tube 56 such that the inside of the inner tube communicates with the inside of the outer tube. A sleeve 51 made of a soft, flexible material such as latex or silicone rubber and having, for example, a thickness of about 0.4 mm, an inner diameter of about 4.7 mm, an outer diameter of about 5 mm, and a length of about 15 mm, is fitted on the outside surface of the inner tube 56 to seal the pore 52. A pressure of at least about 30 mmHg is required to push the plunger a syringe used as a fluid sampling means. Under higher pressures, the sleeve 51 is forced apart A connection port 50 with a Luer hub configuration is integrally formed at the end of inner tube 56 for engagement with the tip of a syringe used as a fluid sampling means. This connection port 50 should preferably be provided with a Luer taper to permit connection with a Luer connector. The junction 57 between outer tube 53 and inner tube 56 may be bonded with an adhesive such as epoxy resin, or may be threaded for threadable engagement. The pore 52 may preferably be provided on the side of inner tube 56 and range from 1.0 to 1.5 mm in diameter. A stop 58 may preferably be provided at the opposite end of inner tube 56 to prevent the sleeve 51 from slipping off under the pressure exerted when the plunger of syringe is pushed in.

In addition, the switching means may be any suitable valve or cock as long as it can select one of a plurality of inflow ports. A three-way stopcock as shown in FIG. 6 and used routinely in medicine is preferable. The present invention also encompasses the use of forceps which clamp the A and V lines. The foreceps may be alternately released on the line from which the sample is to be taken.

The adaptor 38 connected to the blood sampling portion 35 in the sampling line 31 may preferably be designed to ensure that the tip of the syringe 37 be easily and reliably attached, and yet prevent detachment of the syringe under arterial blood pressure. The adaptor is generally provided with a tapered engaging surface and equipped with a locking mechanism to prevent detachment.

The sampling lines at the inflow and discharge portions thereof are connected via connectors to the lines through which flow the fluids to be sampled. Of particular importance is that the connector to the arterial blood line is not disconnected under the arterial pressure (maximum of 300 mmHg).

The operation of the fluid sampling device of the present invention is described as being applied to the oxygenator circuit shown in FIG. 1.

First, the blood inflow portion 34 is connected to the V line in the example shown in FIG. 3; and to the A line in the example shown in FIG. 4. In the example in FIG. 5, the blood inflow portions 34 are connected to both the A and V lines while the switching means 39 selectively communicates the sampling device with the line from which a sample is to be collected. In either example, the blood discharge portion 36 is connected to the V line or the cardiotomy reservoir (CR) 4. In this setup, the blood to be sampled arrives at the inlet of the upstream check valve 32.

A blood sample is collected by attaching syringe 37 in adaptor 38. Suction is applied by the syringe to cause the blood to pass through check valve 32 and enter syringe 37. However, this blood has been held in blood inflow portion 34 and therefore is not sufficiently fresh for blood testing. This unfresh blood should thus be discharged by emptying the syringe. This blood cannot flow towards check valve 32, but is directed to check valve 33 before being returned to the V line side, i.e., the V line, venous reservoir (VR), or cardiotomy reservoir (CR) through blood discharge portion 36. The priming volume of blood inflow portion 34 in sampling line 31 is generally 3 to 8 c.c., and the capacity of the syringe used is 2.5 c.c. Three to four pumps by the syringe are thus required to collect a sample of fresh blood. Even if air should enter the line while this is going on, blood containing air does not flow back toward the blood inflow portion. Thus, even when arterial blood is sampled, there is absolutely no chance of air being introduced into the arterial blood. After several pumps, the required volume of fresh blood is collected in the syringe, completing the sampling process. Even when blood is sampled frequently, samples of fresh blood can be collected merely by fitting a syringe to the adaptor 38, pumping the syringe several times, and thereafter collecting the required volume of blood.

If a connector designed for a maximum arterial pressure of at least 300 mmHg and preferably at least 500 mmHg is connected to the A line, it will never dissociate, preventing blood from spurting out. If the line opening pressure of the check valve is 500 mmHg or higher, arterial blood can be prevented from flowing into the syringe except during aspiration, preventing blood from dripping out at times other than during sample collection.

As compared with conventional devices, the sampling device for medical use of the present invention has many advantages, as described below.

(1) The device of the invention is applicable to blood sample collection from an arterial line without the risk of air entry into the arterial line.

(2) Unlike conventional devices, the device of the invention does not require the complicated operation of a three-way stopcock, permitting the reliable collection of blood samples for testing even by inexperienced users without inviting error.

(3) The procedure may be carried out safely within easy reach without the inconvenience of having to bend down and reach way back with the hand, as conventional devices require, for example, during use on circuits that drain venous blood by gravity.

(4) Fluid may be sampled with great and equal ease whether samples are to be collected from just one fluid line or from several lines.

(5) If the line opening pressure of the check valve is 300 mmHg or more, there is no dripping of blood from the syringe adaptor when the syringe is not attached, even during arterial blood sample collection.

What is claimed is:

1. In combination with an extracorporeal blood circuit having an upstream venous line, a downstream arterial line, and an oxygenator inserted therebetween so that unoxygenated blood flows through the venous line into the oxygenator and oxygenated blood flows from the oxygenator through the arterial line, a blood sampling device comprising:
   a first sampling line in fluid communication with said arterial line;
   a second sampling line in fluid communication with said venous line;
   a discharge line in fluid communication with said venous line;
   switching means having an inlet side coupled to said first and second sampling lines and an outlet side coupled to said discharge line for selectively communicating at one time only one of said first and second sampling lines to said discharge line;
   a fluid line coupled between said sampling and discharge lines and including two check valves arranged in series in said fluid line between said switching means and said discharge line for passing fluid through said fluid line only in a given direction from said sampling lines to said discharge line, one of said two check valves being an upstream check valve having an opening pressure of at least 300 mmHg, with pressure across said check valves, including said opening pressure, being the difference between the pressures at the upstream and the downstream regions of the respective check valves;
   each said check valve comprising an outer tube having an outlet port for blood at one end and closed at the other end, an inner tube extended into the outer tube through its closed other end and having a closed one end located within the outer tube and an inlet for blood at the other end, at least one pore perforated in the side wall of the inner tube, and a flexible sleeve normally fitted over the inner tube to cover the pore and being displaceable when a pressure is applied across the sleeve to allow blood passage from the interior of the inner tube to that of the outer tube through the pore; and
   adaptor means located in said fluid line between said two check valves and including attachment means for permitting a fluid-tight attachment of a sampler having a pumping function to said adaptor means.

2. The blood sampling device of claim 1, wherein said sampler having a pumping function is a syringe.

* * * * *

UNITED STATES PATENT AND TRADEMARK OFFICE
CERTIFICATE OF CORRECTION

PATENT NO. :  4,658,655
DATED       :  April 21, 1987
INVENTOR(S) :  Michio KANNO It is certified that error appears in the above-identified patent and that said Letters Patent is hereby corrected as shown below:

COLUMN 2, line 21, "permits" should read --permit--;

COLUMN 2, line 47, "limination" should read --limitation--;

COLUMN 5, line 35, after "plunger", insert --of--;

line 37, after "apart", insert --from the inner tube. Inner tube 56 is bonded to the outer tube 53.--.

Signed and Sealed this

Fifth Day of April, 1988

*Attest:*

DONALD J. QUIGG

*Attesting Officer*  *Commissioner of Patents and Trademarks*